United States Patent
Wilson et al.

(10) Patent No.: US 9,675,000 B2
(45) Date of Patent: Jun. 13, 2017

(54) OPTICAL FLOW SENSING APPLICATION IN AGRICULTURAL VEHICLES

(71) Applicant: Raven Industries, Inc., Sioux Falls, SD (US)

(72) Inventors: Edwin Ernest Wilson, Round Rock, TX (US); Robert Leonard Nelson, Jr., Austin, TX (US); David Anthony Fowler, Austin, TX (US)

(73) Assignee: Raven Industries, Inc., Sioux Falls, SD (US)

( * ) Notice: Subject to any disclaimer, the term of this patent is extended or adjusted under 35 U.S.C. 154(b) by 0 days.

(21) Appl. No.: 14/706,867

(22) Filed: May 7, 2015

(65) Prior Publication Data

US 2015/0319911 A1 Nov. 12, 2015

Related U.S. Application Data

(60) Provisional application No. 61/991,334, filed on May 9, 2014.

(51) Int. Cl.
*A01B 69/00* (2006.01)
*G06T 7/00* (2017.01)
(Continued)

(52) U.S. Cl.
CPC ............ *A01B 69/00* (2013.01); *A01B 69/001* (2013.01); *B60R 1/00* (2013.01); *G06K 9/00* (2013.01);
(Continued)

(58) Field of Classification Search
CPC ... G01B 11/2513; G01B 11/25; G01B 11/272; A01B 69/00; A01B 69/008; H04N 9/045;
(Continued)

(56) References Cited

U.S. PATENT DOCUMENTS 7,916,898 B2 * 3/2011 Anderson ............ A01B 69/008
250/334
8,844,838 B2 9/2014 Funseth et al.
(Continued)

FOREIGN PATENT DOCUMENTS

WO WO-2015171947 A1 11/2015

OTHER PUBLICATIONS

"International Application Serial No. PCT/US2015/029776, International Preliminary Report on Patentability mailed Nov. 24, 2016", 7 pgs.
(Continued)

*Primary Examiner* — Behrang Badii
(74) *Attorney, Agent, or Firm* — Schwegman Lundberg & Woessner, P.A.

(57) ABSTRACT

System and techniques for optical flow sensing applications in agricultural vehicles are described herein. A plurality of digital images of an agricultural environment can be obtained from a sensor affixed to agricultural equipment. The plurality of digital images can include a first image and a second image, the second image being captured subsequent to the first image. A transformation of a landmark between the first image and the second image can be identified. A degree of motion for the agricultural equipment relative to an environmental target can be calculated based on the transformation of the landmark.

21 Claims, 6 Drawing Sheets

(51) Int. Cl.
*B60R 1/00* (2006.01)
*G06T 7/20* (2017.01)
*G06K 9/00* (2006.01)
*G06T 7/246* (2017.01)
*A01B 69/04* (2006.01)
*H04N 5/232* (2006.01)
*H04N 9/07* (2006.01)
*H04N 9/04* (2006.01)
*A63B 60/42* (2015.01)
*G01N 3/20* (2006.01)
*G01B 11/14* (2006.01)
*F16C 13/00* (2006.01)
*G01B 5/016* (2006.01)
*G01B 11/00* (2006.01)
*G01N 3/04* (2006.01)
*G03F 7/24* (2006.01)
*B05C 1/08* (2006.01)
*G03G 15/08* (2006.01)
*G06T 1/00* (2006.01)
*G03F 7/20* (2006.01)
*A63B 53/10* (2015.01)

(52) U.S. Cl.
CPC ........ *G06K 9/00791* (2013.01); *G06T 7/0004* (2013.01); *G06T 7/20* (2013.01); *G06T 7/246* (2017.01); *A01B 69/008* (2013.01); *A63B 53/10* (2013.01); *A63B 60/42* (2015.10); *B05C 1/08* (2013.01); *F16C 13/00* (2013.01); *G01B 5/016* (2013.01); *G01B 11/007* (2013.01); *G01B 11/14* (2013.01); *G01N 3/04* (2013.01); *G01N 3/20* (2013.01); *G03F 7/24* (2013.01); *G03F 7/70791* (2013.01); *G03G 15/0806* (2013.01); *G06T 1/00* (2013.01); *G06T 2207/30188* (2013.01); *G06T 2207/30252* (2013.01); *H04N 5/23232* (2013.01); *H04N 9/045* (2013.01); *H04N 9/07* (2013.01)

(58) Field of Classification Search
CPC .... H04N 5/23232; H04N 7/18; A01D 34/001; A63B 53/10; A63B 60/42; G06K 9/00; G01N 3/20; G01N 3/04; G06T 1/00; G03F 7/70791; G03F 7/24
See application file for complete search history.

(56) References Cited

U.S. PATENT DOCUMENTS

| | | | |
|---|---|---|---|
| 8,919,676 | B2 | 12/2014 | Funseth et al. |
| 9,073,070 | B2 | 7/2015 | Funseth et al. |
| 9,123,113 | B2 | 9/2015 | Nelson, Jr. |
| 9,266,124 | B2 | 2/2016 | Humpal et al. |
| 2008/0249692 | A1 | 10/2008 | Dix |
| 2008/0275609 | A1 | 11/2008 | Boydell |
| 2010/0063681 | A1 | 3/2010 | Correns et al. |
| 2012/0169869 | A1* | 7/2012 | You .............. A63B 53/10 348/142 |
| 2013/0093923 | A1* | 4/2013 | Imagawa .......... H04N 9/045 348/239 |
| 2014/0085472 | A1 | 3/2014 | Lu et al. |
| 2014/0254861 | A1 | 9/2014 | Nelson, Jr. |
| 2015/0241778 | A1* | 8/2015 | Kato ............. G03F 7/70791 355/67 |
| 2015/0253229 | A1* | 9/2015 | Grondin .......... G01N 3/20 382/107 |
| 2015/0367357 | A1 | 12/2015 | Humpal et al. |
| 2015/0367358 | A1 | 12/2015 | Funseth et al. |
| 2015/0375247 | A1 | 12/2015 | Funseth et al. |
| 2016/0175869 | A1 | 6/2016 | Sullivan et al. |
| 2016/0178422 | A1 | 6/2016 | Humpal et al. |

OTHER PUBLICATIONS

"International Application Serial No. PCT/US15/29776, International Search Report mailed Aug. 10. 2015", 3 pg.

"International Application Serial No. PCT/US15/29776, Written Opinion mailed Aug. 10. 2015", 5 pgs.

* cited by examiner

OPTICAL FLOW SENSING APPLICATION IN AGRICULTURAL VEHICLES

CLAIM OF PRIORITY

This application claims the benefit of priority to U.S. Provisional Patent Application Ser. No. 61/991,334, filed May 9, 2014, which is incorporated herein in its entirety.

TECHNICAL FIELD

This application is generally directed to computer vision and more specifically to an optical flow sensing application in agricultural vehicles.

BACKGROUND

Image based facilitators to agricultural applications, such as navigating agricultural equipment (AEQ), such as an agricultural vehicle (e.g., tractor, truck, etc.) through a field capture images of the agricultural environment. In such applications, a camera, or other sensor, mounted on the AEQ captures electronic representations (e.g., images) of the agricultural environment (e.g., field, grove, etc.), referred to herein as images. These images are then used as inputs into AEQ steering mechanisms—to provide steering variables to the AEQ navigating rows (e.g., crop rows or furrows)—allowing the AEQ to navigate the field without human input.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Optical flow phase correlation techniques in image processing can be used on electronic representations of field (ERFs) (e.g., images) to measure motion of an AEQ moving in relation to a target in the agricultural environment (e.g., a field, orchard, etc.). The relative motion measurement can be used as a general purpose motion sensor using, for example, image data already captured by the AEQ for other purposes. Several examples for this motion sensor can include: a general purpose motion sensor, a motion sensor to provide dead reckoning capabilities to an automated steering system, an implement (e.g., combine, cultivator, planter, etc.) angle sensor, a turnaround row counter, and a non-contact bending moment sensor in rotating shafts.

Figure 1:
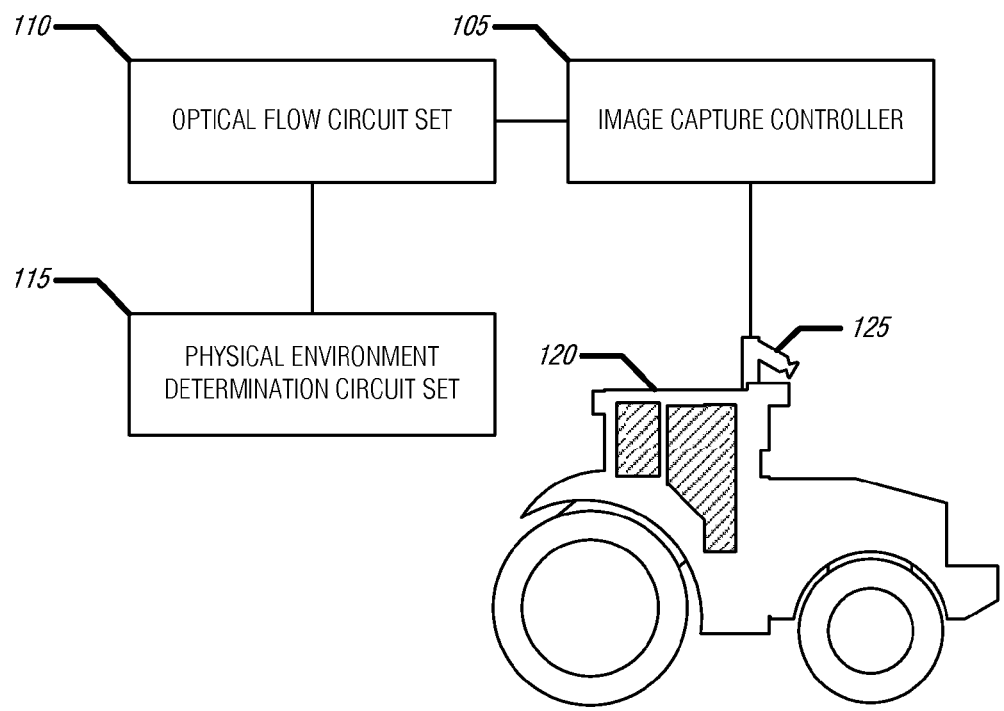
FIG. 1 is a block diagram of an example of a system implementing an optical flow sensing application in agricultural vehicles, according to an embodiment.

FIG. 1 is a block diagram of an example of a system 100 implementing an optical flow sensing application in AEQs. The system 100 includes an AEQ 120 and a sensor 125 (e.g., a camera). The system 100 can also include an image capture controller 105 (e.g., communicatively coupled to the sensor 125), an optical flow circuit set 110, and a physical environment determination circuit set 115. The image capture controller 105 can include the sensor 125 affixed to the AEQ 120. The image capture controller 105 can be arranged obtain a plurality of digital images of an agricultural environment from the sensor 125. This plurality of digital images can include a first image and a second image, the second image being captured subsequent to the first image.

The optical flow circuit set 110 can identify a transformation of a landmark between the first image and the second image, the landmark being common to the first image and the second image.

The physical environment determination circuit set 115 can calculate a degree of motion for the AEQ 120 relative to a target in the agricultural environment based on the transformation of the landmark. For example, the physical environment determination circuit set 115 can calculate a varying angle between the AEQ 120 and a target to determine a translation of the AEQ 120 between the first image and the second image to determine how far the AEQ 120 has traveled. The degree of motion can be relative to a fixed target or a moving target. A fixed target is fixed with respect to the agricultural environment, such as a building, crop row, etc. A moving target is moving within the agricultural environment, such as a vehicle, animal, etc.

In an example, to calculate the degree of motion can include the physical environment circuit set 115 arranged to determine at least one of rotational motion (e.g., pitch, yaw, roll), scale, or two dimensional translation of the AEQ 120 relative to the agricultural environment. The degree of motion can be course over ground (COG) (i.e., a two-dimensional translation of the object from a first position to a second position). COG can include an angle of motion (i.e., a change in the direction to which the object points) or a distance traveled.

In an example, the sensor 125 can be affixed to the AEQ 120 with a static (e.g., unchanging, fixed, etc.) distance or a static angle relative to the AEQ 120. That is, the distance and angle are invariant between the sensor 125 and the AEQ 120 as the AEQ 120 moves (e.g., pitches, rolls, etc.). In an example, the system 100 can include a steering input circuit set arranged to obtain a track angle error (TKE) or a cross-track distance (XTK) for an AEQ 120 steering solution. In this example, the agricultural environment can include a crop row that is the target of the steering solution (e.g., the AEQ 120 is to travel down the row). The steering input circuit set can be arranged to provide updated TKE or XTK values by respectively modifying the previous TKE or XTK distance using COG and distance traveled. In an example, to more efficiently use processing resources, the TKE or XTK can be calculated from the plurality of images. That is, the same images can both be used for the steering solution and the system 100.

The motion sensor described herein can be used in a number of applications. An example application is substituting for a primary steering mechanism—such as that described in U.S. Patent Publication No. 2014/0254861— that is briefly unavailable. In an example, the last TKE or XTK can be used as a waypoint. The relative motion sensor can measure the object's motion with respect to the ground, for example, to determine the relative motion of the object. This relative motion can be used to supply additional TKE or XTK values if, for example, the primary steering mechanism has ceased providing these values in a timely manner. In an example, a timely manner is at least every tenth of a second. In an example, the supplemental TKE or XTK values can be determined by plotting a line between the COG object center, recalculating the angle between the crop row center and the line, or simply subtracting the movement component towards the desired row from the last XTK. In an example, the same plurality of images is used by both the primary steering mechanism and this motion sensor. Thus, additional resource efficiencies can be achieved.

Figure 3A:
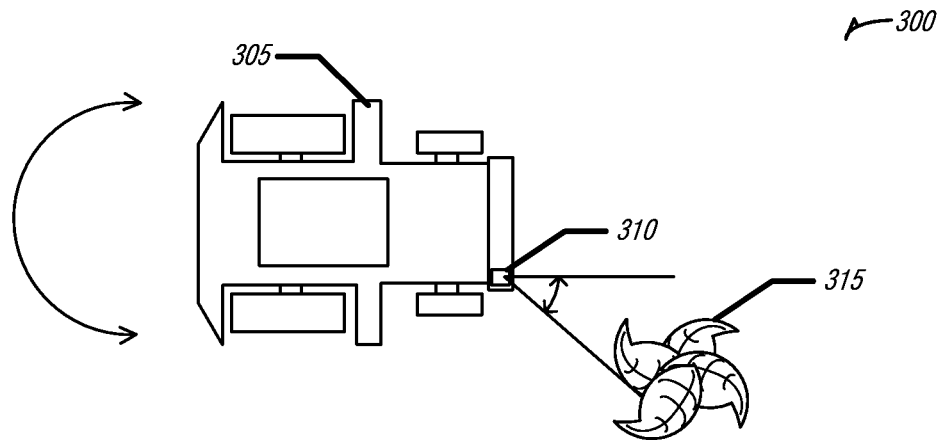
FIGS. 3A-3C illustrate a number of motion determinations that can be made via the described motion sensor, according to an embodiment.
Figure 3B:
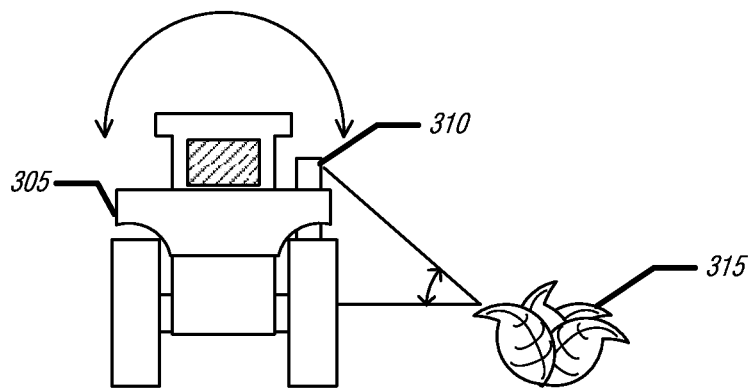
Figure 3C:
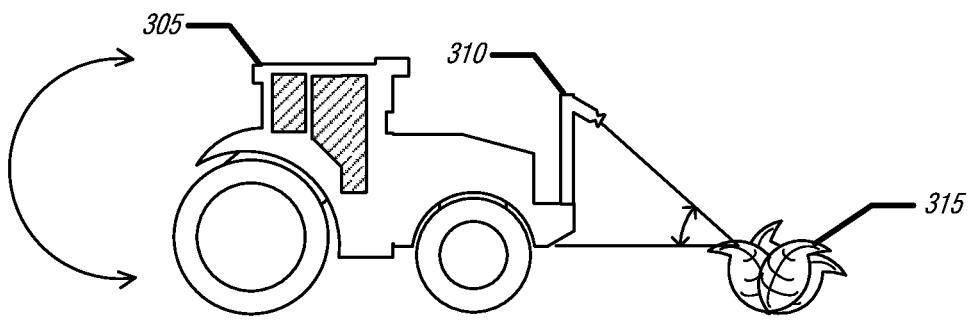

In an example, the sensor 125 can be affixed to the longitudinal axis of the AEQ 120 and angled towards a surface upon which the AEQ 120 is moving, such as a field. In this example, the degree of motion calculated by the physical environment circuit set 115 is the pitch of the AEQ 120. FIG. 3C illustrates just such an example.

In an example, the sensor 125 can be affixed with an angle perpendicular to the longitudinal axis of the AEQ 120. In this example, the degree of motion calculated by the physical environment circuit set 115 is the roll of the AEQ 120. FIG. 3B illustrates just such an example.

In an example, the sensor 125 can be vary between fixation or angle points to capture different motions of the AEQ 120 at different points in time. FIGS. 3A, 3B, and 3C respectively illustrate AEQ 120 motions of yaw, roll, and pitch.

Figure 4A:
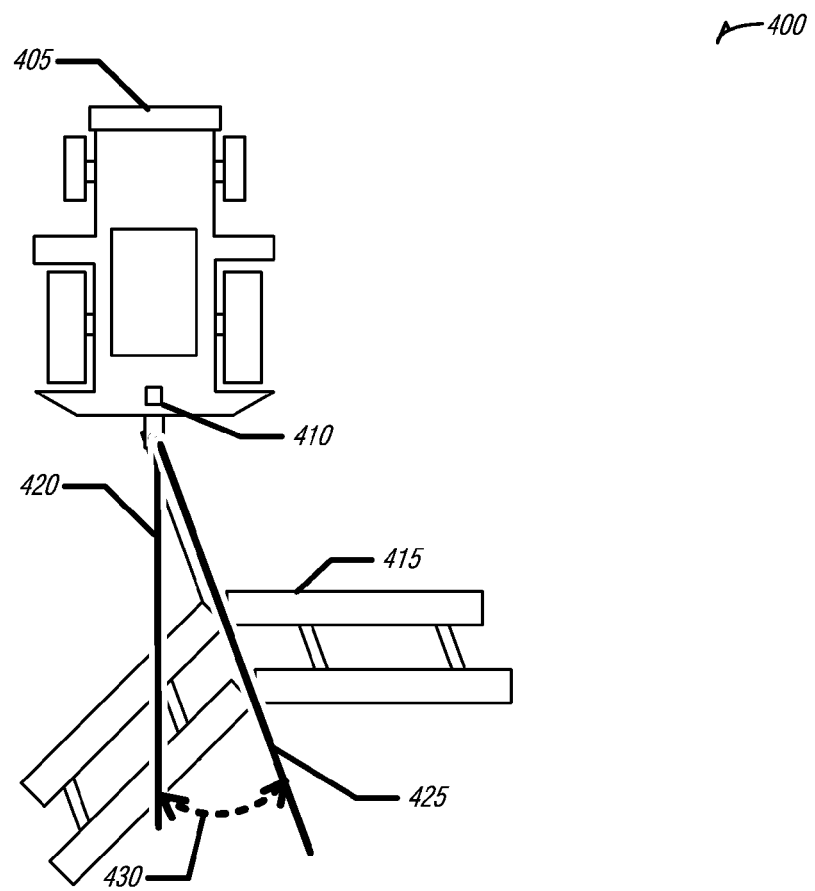
FIGS. 4A and 4B illustrate an example of implement angle or bending moment measurement, according to an embodiment.

In an example, the agricultural environment can include an object. In this example, the degree of AEQ 120 motion calculated by the physical environment circuit set 115 can include a degree of motion between the AEQ 120 and the object. In an example, the object is an implement (e.g., planter, fertilizer, combine, etc.). In this example, the implement can be affixed to the AEQ 120 at a fixation point. Also in this example, the degree of motion calculated by the physical environment circuit set 115 can be an angle between the AEQ 120 and the implement at the fixation point. Such an example is illustrated in FIG. 4A. In an example, the physical environment circuit set 115 is also arranged to measure a deformation of a shaft affixing the implement to the AEQ 120. In this example, the deformation is measured between measureable changes in the shaft between the first image and the second image. In an example, the physical environment circuit set 115 can be arranged to convert the measured deformation into a bending moment measurement.

In an example application, the motion between the AEQ 120 and the object can be constrained, such as when the object is tethered to the AEQ 120 with a limited range of relative motion. A tractor and implement are respectively examples of the AEQ 120 and object where this can be true. In this application, relative motion between the AEQ 120 and the object can provide useful information for both steering applications, as well as for safety or asset protection. For example, an angle between a center line of the fixation point (e.g., line 420 in FIG. 4) and the shaft of the implement to the fixation point (e.g., line 425) can be used to determine how the implement is trailing the AEQ 120. This information can be used, for example, to augment steering calculations to achieve a desired implement trailing angle for a variety of purposes. Further, the angle itself, of a measured deformation in the shaft, can provide information to determine the bending moment upon the shaft. This can be used to protect people and assets by preventing shaft breaks, for example, or simply providing a more accurate use measure for maintenance purposes.

In an example, the physical environment circuit set 115 can be arranged to measure a fill level of a container in the agricultural environment. In the example, the top of the material being deposited or removed from the container is the object. Accordingly, in this example, the degree of motion calculated by the physical environment circuit set 115 is relative to the object (e.g., the top of the material). This motion is relative to the perspective of the sensor 125 affixed to the AEQ 120 rather than relative to the AEQ's motion in the environment itself. In an example, the degree of motion calculation includes determining a scale of the object. This scale can then be used to measure the fill level. For example, a fixed perspective of the sensor 125 may skew the scene towards a vanishing point. Thus, the farther away the top of the material, the smaller it will seem to the sensor 125. The captured portion of an image corresponding to the top of the material can be scaled to fit a reference shape (e.g., circumference of a cylindrical container). The magnitude, and possible sign, of that scaling can indicate, with foreknowledge of the sensing characteristics of the sensor 125, how full the container is.

In an example, the physical environment circuit set 115 can be arranged to use the degree of motion between the AEQ 120 and the object as input in a steering solution to maintain a constant distance between the AEQ 120 and the object. For example, the AEQ 120 can be maintained at a constant distance from another AEQ navigating a parallel row. In an example, the degree of motion between the AEQ 120 and the object is an angle. For example, if the angle between the AEQ 120 and the object, another AEQ changes, and a straight row is being navigated, the magnitude and direction of the change can provide a necessary course correction to the steering solution.

In an example, the physical environment circuit set 115 can be arranged to obtain a target row. In this example, the agricultural environment includes a plurality of rows along with the target row. Also in this example, AEQ 120 motion is relative to rows in the plurality of rows (e.g., the AEQ 120 is moving parallel to the rows). Finally, in this example, the target row is different than the row the AEQ is currently moving down. The physical environment circuit set 115 can be arranged to identify a beginning of a turn towards the target row. The physical environment circuit set 115 can be arranged to navigate to the target row through the turn using the calculated degree of motion for the AEQ 120 relative to the agricultural environment. For example, the target can be the desired crop row after a turn at the end of the field. So steering applications, such as that described in U.S. Patent Publication No. 2014/0254861, work within rows, but may not work outside of a row. Some steering applications can simply fail due to external interference—such as satellite or radio tower based navigation solutions. In these examples, the motion sensor can be used to facilitate dead reckoning by providing relative motion information for the AEQ 120 without input from other sensors. The dead reckoning can be used to steer to the target row when the AEQ 120 has reached the end of the field. In an example, the target row can be automatically determined based on object parameters, such as turning radius of the AEQ 120.

In an example, to obtain the target row, the physical environment circuit set 115 can be arranged to divide a width of an implement turn diameter by a row width to determine a row count. In this example, the implement is the AEQ 120 or is tethered to the AEQ 120. The physical environment circuit set 115 can arranged to select a row that is a row distance equivalent to the row count from the current row of the AEQ 120. In an example, the physical environment circuit set 115 is arranged to receive an indication from a use that a turn has begun (e.g., to ascertain the target row and begin the steering maneuver). In an example, the physical environment circuit set 115 is arranged to determine that the turn has begun by receiving an indication that automatic steering has been disengaged. In this example, the automatic steering is can be under the control of another system, such as satellite navigation, rather than the system 100. In an example, the physical environment circuit set 115 is arranged to receive a last good automatic steering solution at the beginning of the turn. Thus, the system 100 can navigate, via dead reckoning, to the target row with confidence that the AEQ 120 is at the physical location from which the target row was selected.

Figure 2A:
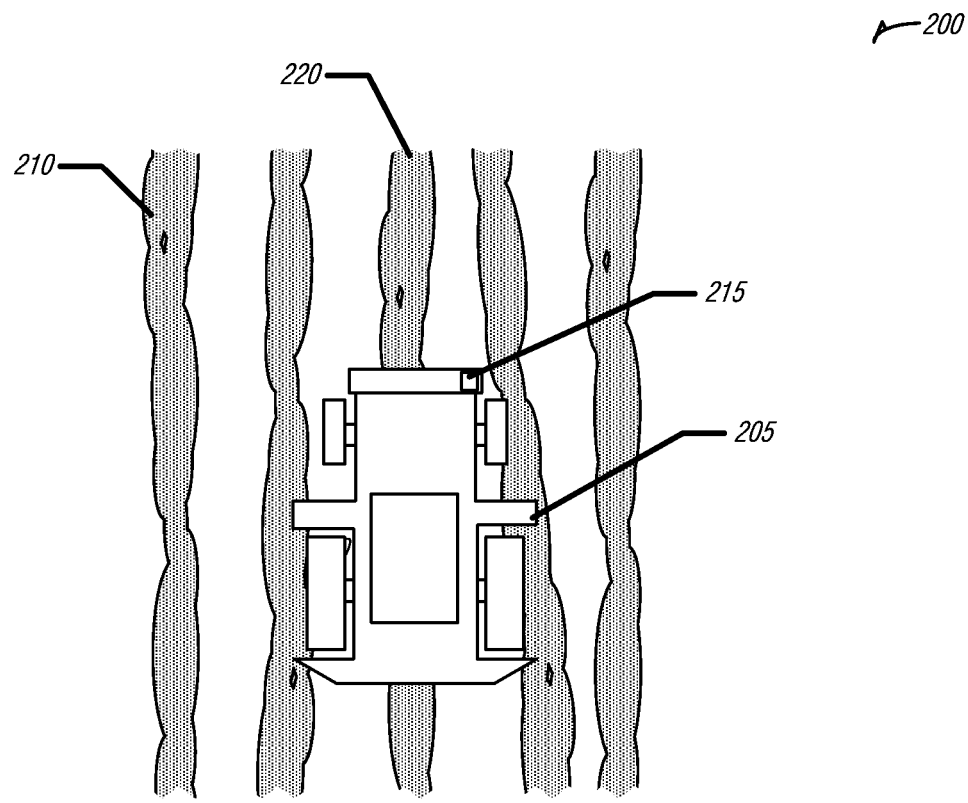
FIGS. 2A and 2B illustrate an environment in which optical flow data can be collected and used, according to an embodiment.
Figure 2B:
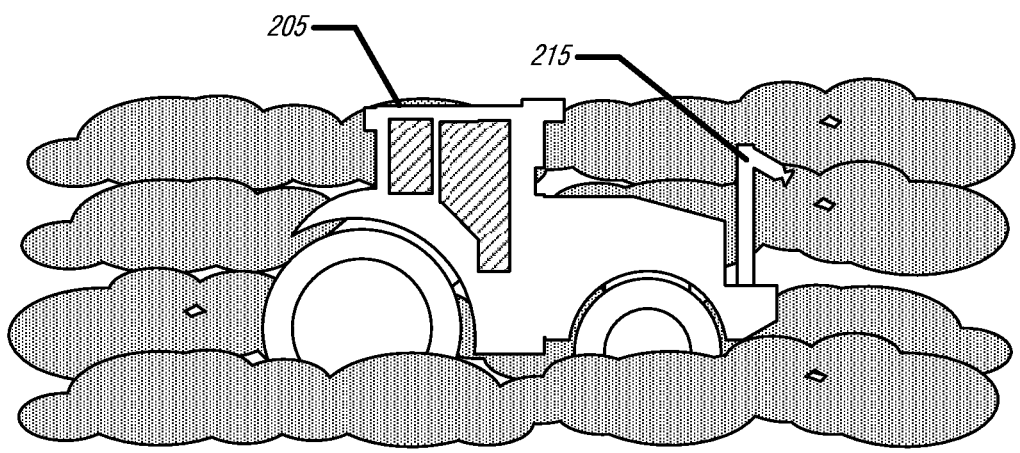

FIGS. 2A and 2B illustrate an environment 200 in which optical flow data can be collected and used. FIG. 2A is a top-down view and FIG. 2B is a profile view of the environment 200, including the AEQ 205 and the sensor 215. Crop row 220 is a current crop row. Crop row 210 is a target crop row for the turning techniques described above.

FIGS. 3A-3C illustrate an example 300 of a number of motion determinations that can be made via the described motion sensor. FIG. 3A illustrates yaw, FIG. 3B illustrates roll, and FIG. 3C illustrates pitch of the object 305 and affixed sensor 310. Each of these are calculable degrees of motion from the system 100 relative to an environmental target 315 based on, for example, the varying angle between the sensor 310 so affixed to the AEQ 305 and the target 315.

Figure 4B:
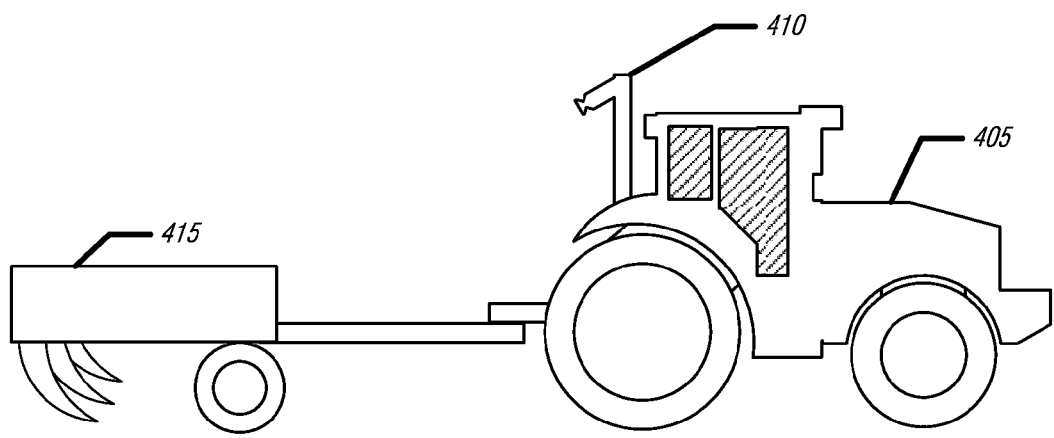

FIGS. 4A and 4B illustrate an example 400 of implement angle or bending moment measurement. FIG. 4A is a top-down view and FIG. 4B is a profile view of the example 400. The AEQ 405 is affixed to the implement 415. The sensor 410 is position so as to capture the deviation 430 of the implement 415 with shaft line 425 and a line 420 extending back from the fixation point. In an example, the line 425 is marked in the sensor 410 to facilitate examination of the deviation 430.

Figure 5:
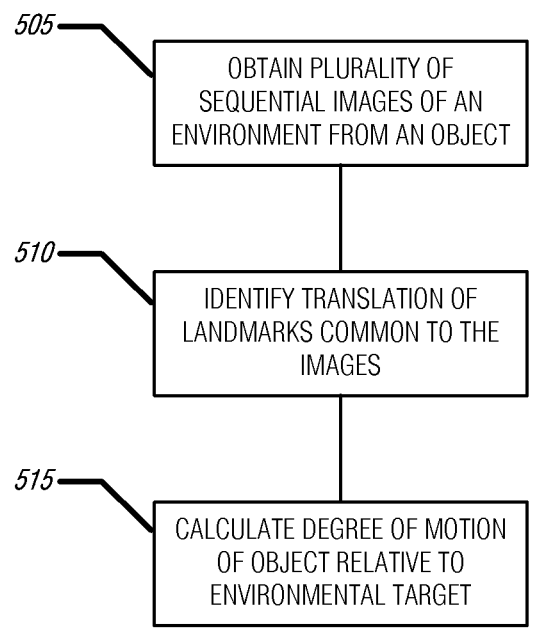
FIG. 5 is a block diagram of an example of a method implementing an optical flow sensing application in agricultural vehicles, according to an embodiment.

FIG. 5 is a block diagram of an example of a method implementing an optical flow sensing application in AEQs. Operations of the method 500 are carried out on computing hardware, such as those components described above with respect to FIG. 1, or below with respect to FIG. 6.

At operation 505 a plurality of digital images of an environment of an object (e.g., an AEQ) from a sensor affixed to the object can be obtained. The plurality of digital images includes a first image and a second image, where the second image being captured subsequent to the first image.

At operation 510 a translation of landmarks that are common to the first image and the second image between the first image and the second image can be identified. Landmark identification can take many forms, including image registration techniques, color, brightness, or other types of image recognition techniques.

At operation 515 a degree of motion for the object relative to an environmental target based on the translation of the landmarks can be calculated.

In an example, calculating the degree of motion can include calculating at least one of rotation, scale, or two dimensional translation of the object relative to the target. In an example, the sensor is affixed with a static distance and static angle relative to the object. In this example, the static distance and angle are invariant with respect to the object as the object moves. In this example, the degree of motion is a course over ground (COG) and distance applied to a planar representation of a surface upon which the object is moving, the COG and distance determined from the rotation, scale, and two dimensional translation of the object relative to the target.

In an example, the sensor is affixed to the longitudinal axis of the object and angled toward a surface upon which the object is moving. In this example, the degree of motion is object pitch relative to the surface. In an example, the sensor is affixed with an angle perpendicular to the longitudinal axis of the object. In this example, the degree of motion is object roll relative to a surface upon which the object is moving.

In an example, the target is a second object affixed to the first object at a fixation point. In this example, the degree of motion is an angle between the object and the second object. In an example, the second object is an implement, such as a cultivator, planter, spreader, etc.

In an example, a deformation of a shaft between the object and the second object can be measured. The deformation can be converted into a bending moment measurement. For example, given physical properties of the shaft, including points of implement attached, it can be determined what force would produce the observed deformation.

In an example, the target can be the surface of a material being deposited into a container. In this example, the degree of motion is relative to the surface. Thus, using scale, for example, a rate of fill, or a total amount filled, can be determined.

In an example, the target can be moving within the environment, and the degree of motion is a differential used as input to a steering solution to maintain a constant distance between the object and the target.

At additional operation 520, a track angle error and XTK for a crop vehicle steering solution can be obtained. The object is the crop vehicle and the target is a crop row that is the object of the steering solution. In an example, the track angle error and the XTK are calculated from images taken from the plurality of images.

At additional operation 525, updated track angle error and XTK values can be provided by modifying the track angle error and XTK using the COG and distance from operation 515.

At additional operation 530, the target can be a target row. In an example, the environment can include a plurality of rows including the target row. In an example, the object motion is relative to rows in the plurality of rows and the target row is different than the current row. In this example, the beginning of a turn can be identified. In this example, the target row can be navigated to by the object through the turn via the degree of motion. This can operate as a dead reckoning alternative to steering solutions that, for example, may not operate outside of the rows. In this example, a model of the environment can be maintained. The object's position on the model can be updated by the degree of motions parameters.

In an example, obtaining the target row can include dividing a width of an implement by a row width to determine a row count. In this example, the implement is the object or affixed to the object. Then a row that is a row distance equivalent to the row count from a current row of the object can be selected as the target row. In this manner, an automatic row counter is implemented. This can be used to determine the target for the end-of-row turn described above. In an example, obtaining the target row can include receiving identification of the target row from a user via a user interface. In an example, identifying the beginning of the turn includes receiving an indication from a user that a turn has begun. In an example, identifying the beginning of the turn includes receiving an indication that automatic steering has been disengaged. In an example, identifying the beginning of the turn includes receiving a last good automatic steering solution.

Figure 6:
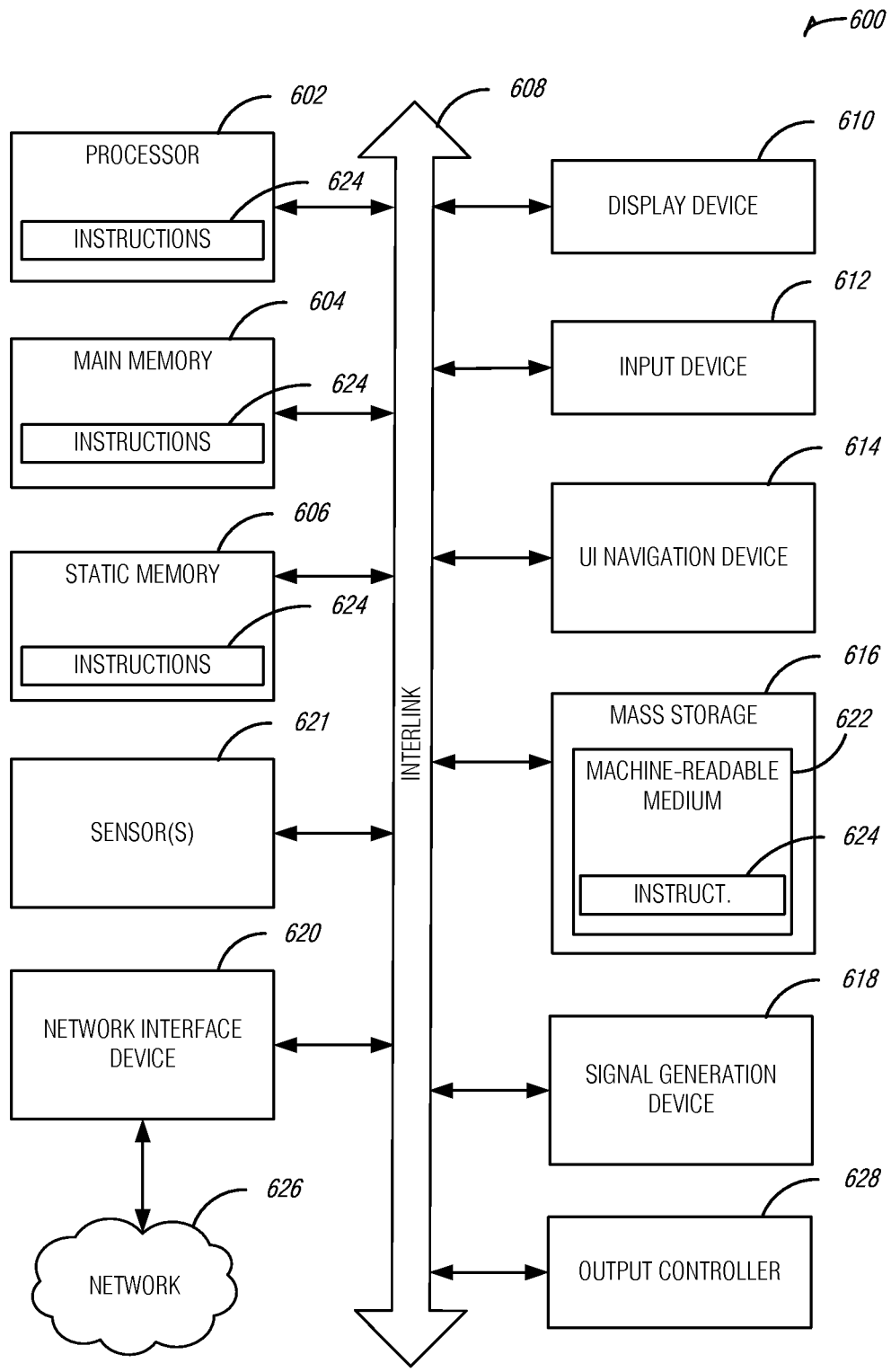
FIG. 6 is a block diagram illustrating an example of a machine upon which one or more embodiments may be implemented.

FIG. 6 illustrates a block diagram of an example machine 600 upon which any one or more of the techniques (e.g., methodologies) discussed herein may perform. In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Additional Notes & Examples

Example 1 includes subject matter (such as a device, apparatus, or machine) comprising: an image capture control to obtain a plurality of digital images of an agricultural environment from a sensor affixed to agricultural equipment (AEQ), the plurality of digital images including a first image and a second image, the second image being captured subsequent to the first image; an optical flow circuit set to identify a transformation of landmarks between the first image and the second image, the landmarks being common to the first image and the second image; and a physical environment circuit set to calculate a degree of motion for the AEQ relative to an environmental target based on the transformation of the landmarks.

In Example 2, the subject matter of Example 1 may include, wherein to calculate the degree of motion includes the physical environment circuit set to determine at least one of rotation, scale, or two dimensional translation of the object relative to the environment.

In Example 3, the subject matter of any one of Examples 1 to 2 may include, wherein the sensor is affixed with a static distance and static angle relative to the AEQ, the static distance and angle being invariant with respect to the AEQ as the AEQ moves, and wherein the degree of motion is a course over ground (COG) and distance applied to a planar representation of a surface upon which the AEQ is moving, the COG and distance determined from the rotation, scale, and two dimensional translation of the object relative to the environment.

In Example 4, the subject matter of any one of Examples 1 to 3 may include, a steering input circuit set to: obtain a track angle error and cross-track distance for an AEQ solution, wherein the agricultural environment includes a crop row that is a target of the steering solution; and provide updated track angle error and cross-track distance values by modifying the track angle error and cross-track distance using the COG and distance.

In Example 5, the subject matter of any one of Examples 1 to 4 may include, wherein the track angle error and the cross-track distance are calculated from images taken from the plurality of images.

In Example 6, the subject matter of any one of Examples 1 to 5 may include, wherein the sensor is affixed to the longitudinal axis of the AEQ and angled toward a surface upon which the AEQ is moving, and where the degree of motion is AEQ pitch relative to the surface.

In Example 7, the subject matter of any one of Examples 1 to 6 may include, wherein the sensor is affixed with an angle perpendicular to the longitudinal axis of the AEQ, and where the degree of motion is AEQ roll relative to a surface upon which the AEQ is moving.

In Example 8, the subject matter of any one of Examples 1 to 7 may include, wherein the agricultural environment includes an object, and wherein calculating the degree of motion for the AEQ relative to the agricultural environment includes determining a degree of motion between the AEQ and the object.

In Example 9, the subject matter of any one of Examples 1 to 8 may include, wherein the object is an implement, wherein the implement is affixed to the AEQ at a fixation point, and wherein the degree of motion is an angle between the AEQ and the implement at the fixation point.

In Example 10, the subject matter of any one of Examples 1 to 9 may include, wherein the physical environment circuit set is to: measure a deformation of a shaft affixing the implement to the AEQ between the first image and the second image; and convert the deformation into a bending moment measurement.

In Example 11, the subject matter of any one of Examples 1 to 10 may include, wherein the physical environment circuit set is to measure a fill level of a container in the environment, wherein the top of material filling the container is the object, and wherein the degree of motion is relative to the object.

In Example 12, the subject matter of any one of Examples 1 to 11 may include, wherein to calculate the degree of motion includes the physical environment circuit set to determine a scale of the object, and wherein to measure the fill level of the container in the environment includes using the scale.

In Example 13, the subject matter of any one of Examples 1 to 12 may include, wherein the physical environment circuit set is to use the degree of motion between the AEQ and the object as input into a steering solution to maintain a constant distance between the AEQ and the object.

In Example 14, the subject matter of any one of Examples 1 to 13 may include, wherein the degree of motion between the AEQ and the object is an angle.

In Example 15, the subject matter of any one of Examples 1 to 14 may include, wherein the physical environment circuit set is to: obtain a target row, wherein the agricultural environment includes a plurality of rows including the target row, wherein AEQ motion is relative to rows in the plurality of rows, and wherein the target row is a different than a row in the plurality of rows down which the AEQ is currently moving; identify a beginning of a turn towards the target row; and navigate to the target row through the turn via the calculated degree of motion for the AEQ relative to the agricultural environment.

In Example 16, the subject matter of any one of Examples 1 to 15 may include, wherein to obtain the target row includes the physical environment circuit set to: divide a width of an implement by a row width to determine a row count, wherein the implement is the AEQ or affixed to the AEQ; and select a row that is a row distance equivalent to the row count from a current row of the AEQ.

In Example 17, the subject matter of any one of Examples 1 to 16 may include, wherein to obtain the target row includes physical environment circuit set to receive identification of the target row from a user via a user interface.

In Example 18, the subject matter of any one of Examples 1 to 17 may include, wherein to identify the beginning of the turn includes the physical environment circuit set to receive an indication from a user that a turn has begun.

In Example 19, the subject matter of any one of Examples 1 to 18 may include, wherein to identify the beginning of the turn includes the physical environment circuit set to receive an indication that automatic steering has been disengaged.

In Example 20, the subject matter of any one of Examples 1 to 19 may include, wherein to identify the beginning of the turn includes the physical environment circuit set to receive a last good automatic steering solution.

Example 21 includes, or may optionally be combine with the subject matter of any of claims 1 to 20 to include, subject matter (such as a method, means for performing acts, machine readable medium including instructions that when performed by a machine cause the machine to performs acts, or an apparatus to perform) comprising: obtaining a plurality of digital images of an agricultural environment from a sensor affixed to agricultural equipment (AEQ), the plurality of digital images including a first image and a second image, the second image being captured subsequent to the first image; identifying a transformation of landmarks between the first image and the second image, the landmarks being common to the first image and the second image; and calculating a degree of motion for the AEQ relative to an environmental target based on the transformation of the landmarks.

In Example 22, the subject matter of Example 21 may include, wherein calculating the degree of motion includes determining at least one of rotation, scale, or two dimensional translation of the object relative to the environment.

In Example 23, the subject matter of any one of Examples 21 to 22 may include, wherein the sensor is affixed with a static distance and static angle relative to the AEQ, the static distance and angle being invariant with respect to the AEQ as the AEQ moves, and wherein the degree of motion is a course over ground (COG) and distance applied to a planar representation of a surface upon which the AEQ is moving, the COG and distance determined from the rotation, scale, and two dimensional translation of the object relative to the environment.

In Example 24, the subject matter of any one of Examples 21 to 23 may include obtaining a track angle error and cross-track distance for an AEQ solution, wherein the agricultural environment includes a crop row that is a target of the steering solution; and providing updated track angle error and cross-track distance values by modifying the track angle error and cross-track distance using the COG and distance.

In Example 25, the subject matter of any one of Examples 21 to 24 may include, wherein the track angle error and the cross-track distance are calculated from images taken from the plurality of images.

In Example 26, the subject matter of any one of Examples 21 to 25 may include, wherein the sensor is affixed to the longitudinal axis of the AEQ and angled toward a surface upon which the AEQ is moving, and where the degree of motion is AEQ pitch relative to the surface.

In Example 27, the subject matter of any one of Examples 21 to 26 may include, wherein the sensor is affixed with an angle perpendicular to the longitudinal axis of the AEQ, and where the degree of motion is AEQ roll relative to a surface upon which the AEQ is moving.

In Example 28, the subject matter of any one of Examples 21 to 27 may include, wherein the agricultural environment includes an object, and wherein calculating the degree of motion for the AEQ relative to the agricultural environment includes determining a degree of motion between the AEQ and the object.

In Example 29, the subject matter of any one of Examples 21 to 28 may include, wherein the object is an implement, wherein the implement is affixed to the AEQ at a fixation point, and wherein the degree of motion is an angle between the AEQ and the implement at the fixation point.

In Example 30, the subject matter of any one of Examples 21 to 29 may include measuring a deformation of a shaft affixing the implement to the AEQ between the first image and the second image; and converting the deformation into a bending moment measurement.

In Example 31, the subject matter of any one of Examples 21 to 30 may include measuring a fill level of a container in the environment, wherein the top of material filling the container is the object, and wherein the degree of motion is relative to the object.

In Example 32, the subject matter of any one of Examples 21 to 31 may include, wherein calculating the degree of motion includes determining a scale of the object, and wherein measuring the fill level of the container in the environment includes using the scale.

In Example 33, the subject matter of any one of Examples 21 to 32 may include using the degree of motion between the AEQ and the object as input into a steering solution to maintain a constant distance between the AEQ and the object.

In Example 34, the subject matter of any one of Examples 21 to 33 may include, wherein the degree of motion between the AEQ and the object is an angle.

In Example 35, the subject matter of any one of Examples 21 to 34 may include obtaining a target row, wherein the agricultural environment includes a plurality of rows including the target row, wherein AEQ motion is relative to rows in the plurality of rows, and wherein the target row is a different than a row in the plurality of rows down which the AEQ is currently moving; identifying a beginning of a turn towards the target row; and navigating to the target row through the turn via the calculated degree of motion for the AEQ relative to the agricultural environment.

In Example 36, the subject matter of any one of Examples 21 to 35 may include, wherein obtaining the target row includes: dividing a width of an implement by a row width to determine a row count, wherein the implement is the AEQ or affixed to the AEQ; and selecting a row that is a row distance equivalent to the row count from a current row of the AEQ.

In Example 37, the subject matter of any one of Examples 21 to 36 may include, wherein obtaining the target row includes receiving identification of the target row from a user via a user interface.

In Example 38, the subject matter of any one of Examples 21 to 37 may include, wherein identifying the beginning of the turn includes receiving an indication from a user that a turn has begun.

In Example 39, the subject matter of any one of Examples 21 to 38 may include, wherein identifying the beginning of the turn includes receiving an indication that automatic steering has been disengaged.

In Example 40, the subject matter of any one of Examples 21 to 39 may include, wherein identifying the beginning of the turn includes receiving a last good automatic steering solution.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for applying optical flow sensing for agricultural vehicles, the system comprising:
   an image capture controller to obtain a plurality of digital images of an agricultural environment from a sensor affixed to agricultural equipment (AEQ), the plurality of digital images including a first image and a second image, the second image being captured subsequent to the first image, the agricultural environment including an object that is an implement affixed to the AE at a fixation point;
   an optical flow circuit set to identify a transformation of a landmark between the first image and the second image, the landmark being common to the first image and the second image; and
   a physical environment circuit set to calculate a degree of motion for the AEQ relative to an environmental target based on the transformation of the landmark, the degree of motion including a degree of motion between the AEQ and the object determined by:
   measuring a deformation of a shaft affixed the implement to the AEQ between the first image and the second image from the degree of motion; and
   converting the deformation into a bending moment measurement.

2. The system of claim 1, wherein to calculate the degree of motion includes the physical environment circuit set to determine at least one of rotation, scale, or two dimensional translation of the object relative to the agricultural environment.

3. The system of claim 2, wherein the sensor is affixed with a static distance and static angle relative to the AEQ, the static distance and angle being invariant with respect to the AEQ as the AEQ moves, and wherein the degree of motion includes a course over ground (COG) and distance applied to a planar representation of a surface upon which the AEQ is moving, the COG and distance determined from the rotation, scale, and two dimensional translation of the object relative to the agricultural environment.

4. The system of claim 3, comprising a steering input circuit set to:
   obtain a track angle error and cross-track distance for an AEQ steering solution, wherein the agricultural environment includes a crop row that is a target of the steering solution; and
   provide updated track angle error and cross-track distance values by modifying the track angle error and cross-track distance using the COG and distance.

5. The system of claim 1, wherein the physical environment circuit set is to use the degree of motion between the AEQ and a second object in the agricultural environment as input into a steering solution to maintain a constant distance between the AEQ and the object.

6. The system of claim 1, wherein the physical environment circuit set is to:
   obtain a target row, wherein the agricultural environment includes a plurality of rows including the target row, wherein the degree of motion includes motion relative to rows in the plurality of rows, and wherein the target row is a different than a row in the plurality of rows down which the AEQ is currently moving;
   identify a beginning of a turn towards the target row; and
   navigate to the target row through the turn via the calculated degree of motion for the AEQ relative to the agricultural environment.

7. The system of claim 1 wherein the shaft is a rotating shaft.

8. A hardware circuit implemented method comprising:
   obtaining a plurality of digital images of an agricultural environment from a sensor affixed to agricultural equipment (AEQ), the plurality of digital images including a first image and a second image, the second image being captured subsequent to the first image, the agricultural environment including an object that is an implement affixed to the AE at a fixation point;
   identifying a transformation of a landmark between the first image and the second image, the landmark being common to the first image and the second image; and
   calculating a degree of motion for the AEQ relative to an environmental target based on the transformation of the landmark, the degree of motion including a degree of motion between the AEQ and the object determined by:
   measuring a deformation of a shaft affixed the implement to the AEQ between the first image and the second image from the degree of motion; and converting the deformation into a bending moment measurement.

9. The method of claim 8, wherein calculating the degree of motion includes determining at least one of rotation, scale, or two dimensional translation of the object relative to the agricultural environment.

10. The method of claim 9, wherein the sensor is affixed with a static distance and static angle relative to the AEQ, the static distance and angle being invariant with respect to the AEQ as the AEQ moves, and wherein the degree of motion includes a course over ground (COG) and distance applied to a planar representation of a surface upon which the AEQ is moving, the COG and distance determined from the rotation, scale, and two dimensional translation of the object relative to the agricultural environment.

11. The method of claim 10, comprising:
obtaining a track angle error and cross-track distance for an AEQ steering solution, wherein the agricultural environment includes a crop row that is a target of the steering solution; and
providing updated track angle error and cross-track distance values by modifying the track angle error and cross-track distance using the COG and distance.

12. The method of claim 8, comprising using the degree of motion between the AEQ and a second object in the agricultural environment as input into a steering solution to maintain a constant distance between the AEQ and the object.

13. The method of claim 8, comprising:
obtaining a target row, wherein the agricultural environment includes a plurality of rows including the target row, wherein the degree of motion includes motion relative to rows in the plurality of rows, and wherein the target row is a different than a row in the plurality of rows down which the AEQ is currently moving;
identifying a beginning of a turn towards the target row; and
navigating to the target row through the turn via the calculated degree of motion for the AEQ relative to the agricultural environment.

14. The method of claim 8, wherein the shaft is a rotating shaft.

15. A set of non-transitory machine readable media including instructions that, when executed by a machine, cause the machine to perform operation comprising:
obtaining a plurality of digital images of an agricultural environment from a sensor affixed to agricultural equipment (AEQ), the plurality of digital images including a first image and a second image, the second image being captured subsequent to the first image, the agricultural environment including an object that is an implement affixed to the AE at a fixation point;
identifying a transformation of a landmark between the first image and the second image, the landmark being common to the first image and the second image; and
calculating a degree of motion for the AEQ relative to an environmental target based on the transformation of the landmark, the degree of motion including a degree of motion between the AEQ and the object determined by:
measuring a deformation of a shaft affixed the implement to the AEQ between the first image and the second image from the degree of motion; and
converting the deformation into a bending moment measurement.

16. The set of machine readable media of claim 15, wherein calculating the degree of motion includes determining at least one of rotation, scale, or two dimensional translation of the object relative to the agricultural environment.

17. The set of machine readable media of claim 16, wherein the sensor is affixed with a static distance and static angle relative to the AEQ, the static distance and angle being invariant with respect to the AEQ as the AEQ moves, and wherein the degree of motion includes a course over ground (COG) and distance applied to a planar representation of a surface upon which the AEQ is moving, the COG and distance determined from the rotation, scale, and two dimensional translation of the object relative to the agricultural environment.

18. The set of machine readable media of claim 17, wherein the operations further comprise:
obtaining a track angle error and cross-track distance for an AEQ steering solution, wherein the agricultural environment includes a crop row that is a target of the steering solution; and
providing updated track angle error and cross-track distance values by modifying the track angle error and cross-track distance using the COG and distance.

19. The set of machine readable media of claim 15, wherein the operations further comprise using the degree of motion between the AEQ and a second object in the agricultural environment as input into a steering solution to maintain a constant distance between the AEQ and the object.

20. The set of machine readable media of claim 15, wherein the operations further comprise:
obtaining a target row, wherein the agricultural environment includes a plurality of rows including the target row, wherein the degree of motion includes motion relative to rows in the plurality of rows, and wherein the target row is a different than a row in the plurality of rows down which the AEQ is currently moving;
identifying a beginning of a turn towards the target row; and
navigating to the target row through the turn via the calculated degree of motion for the AEQ relative to the agricultural environment.

21. The method of claim 15, wherein the shaft is a rotating shaft.

* * * * *